United States Patent [19]

Schneider et al.

[11] Patent Number: 5,412,009
[45] Date of Patent: May 2, 1995

[54] FLAME RETARDANT COMPOUNDS COMPRISING FULLY BROMINATED DIANHYDRIDES

[75] Inventors: Michael J. Schneider, Near Chester; James Gainer, Worsley, both of United Kingdom

[73] Assignee: FMC Corportion (UK) Limited, Manchester, United Kingdom

[21] Appl. No.: 988,069

[22] Filed: Dec. 7, 1992

[30] Foreign Application Priority Data

Dec. 24, 1991 [GB] United Kingdom ............... 9127587

[51] Int. Cl.6 .................................. C08K 5/15
[52] U.S. Cl. ................... 524/109; 528/102; 528/112; 549/241
[58] Field of Search ............. 524/109; 528/112, 102; 549/241

[56] References Cited

U.S. PATENT DOCUMENTS

| | | | |
|---|---|---|---|
| 3,440,277 | 4/1969 | Holland et al. | 549/241 |
| 3,502,609 | 3/1970 | Barie | 528/112 |
| 3,891,633 | 6/1975 | Berlin et al. | 528/112 |
| 4,180,607 | 12/1979 | Sasaki et al. | 528/112 |
| 4,282,136 | 8/1981 | Hunt et al. | 528/112 |

FOREIGN PATENT DOCUMENTS 2525697 12/1976 Germany .

OTHER PUBLICATIONS

Chemical Abstract 102: 113273j, "Halo-3,3',4,4'-benzo-phenonetetracarboxylic dianhydrides".
Chemical Abstract 103: 7446d, "Flame-Retardant Copper-Clad Epoxy Laminates".

Primary Examiner—Frederick Krass
Attorney, Agent, or Firm—Patrick C. Baker; Charles C. Fellows; Robert L. Andersen

[57] ABSTRACT

The invention provides a compound of general formula I

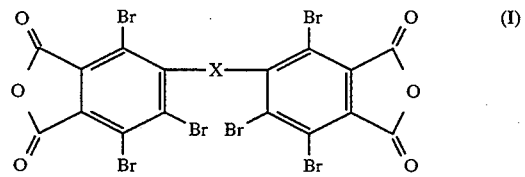

in which X represents a direct bond or a

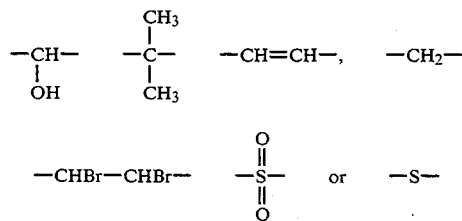

group.

12 Claims, No Drawings

FLAME RETARDANT COMPOUNDS COMPRISING FULLY BROMINATED DIANHYDRIDES

This invention relates to flame retardant compounds and compositions containing them.

Brominated organic compounds are well known to have flame retardant properties and are extensively used for this purpose in a wide variety of materials such as plastics and rubber, and including cellular and foamed materials such as foamed polystyrene and foamed polyurethanes.

The vapor phase mode of action of these compounds relies to a great extent on the thermal stability of the brominated compound in relation to that of the polymer. If the flame retardant compound has too low a thermal stability, i.e. begins to decompose or vaporize at too low a temperature, then it will be exhausted before the polymer itself starts decomposing. If the flame retardant has too high a thermal stability, it will remain in the condensed phase, and will therefore, remain inactive as the polymer decomposes. Thus, it is desirable to have a flame retardant compound whose thermal stability closely matches that of the polymer.

The thermal stability of various known flame retardants is given below, the accepted measure of thermal stability being the temperature in °C. at which there is a 10% loss in weight; ("Thermal Characteristics of Polymer Materials", E. A. Turi, Academic Press, 1981 );

|  | 10% wt. loss at |
| --- | --- |
| decabromodiphenyloxide (DBDPO) | 373° C. |
| octabromodiphenyloxide (OBDPO) | 340° C. |
| bis(2-hydroxyethyl)ether of tetrabromo-bisphenol A | 337° C. |
| octabromodiphenyl oxide | 336° C. |

Of these DBDPO has been extensively used as a flame retardant in ABS (acrylonitrile-butadiene-styrene) rubbers and other similar engineering thermoplastics (ETP) that have a high thermal stability, e.g. HIPS, and therefore, require a high thermal stability flame retardant to match. ABS, for example, shows decomposition to 10% weight loss at about 390° C. (Stanton Redcroft STA 100, 10° C. min.$^{-1}$ 30 ml.min.$^{-1}$ air, sample weight 10±0.02 mg. Iconel crucible). This figure is reasonably closely matched by that of DBDPO at 373° C. However, the use of DBDPO has recently come into question, as it is suspected of forming highly toxic brominated dibenzodioxins and furans upon pyrolysis, and these products have, indeed, been detected in the pyrolysis of polymer systems containing DBDPO.

Octabromodiphenyloxide has been substituted for DBDPO but is less effective as a flame retardant, and is also suspected of forming brominated dibenzo-dioxins and -furans upon pyrolysis.

Thus, a need still exists for flame retardant compounds of high thermal stability and which are not prone to the formation of such toxic substances upon pyrolysis.

We have now, surprisingly, determined that certain brominated anhydrides impart excellent flame retardant properties to a wide range of plastics.

Accordingly, the present invention provides compounds of the general formula (I)

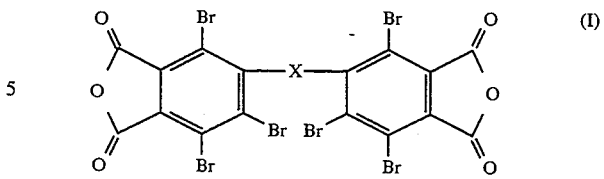

in which X represents a direct bond or a group

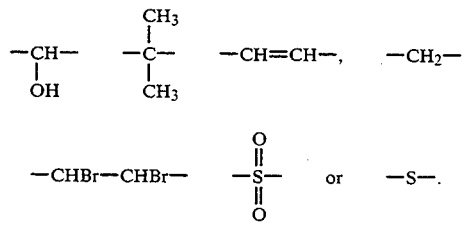

Preferably X represents a direct bond between the two aromatic rings.

The compounds of the invention can be readily prepared by bromination of the corresponding dianhydride. The process may be carried out by treating the dianhydride with bromine under acid conditions and at an elevated temperature. The reaction is preferably carried out under reflux.

The compounds of the invention are useful as flame retardants in a wide variety of polymers including:

1. Polystyrene, poly-(p-methylstyrene) or poly-(α-methylstyrene).
2. Copolymers of styrene or α-methylstyrene with dienes or acrylic derivatives, such as, for example, styrene/butadiene, styrene/acrylonitrile, styrene-/alkyl methacrylate, styrene/maleic anhydride, styrener/butadiene/ethyl acrylate, styrene/acrylonitrile/methyl acrylate; mixtures of high impact strength from styrene copolymers and another polymer, such as, for example, styrene/butadiene/styrene, styrene/isoprene/-styrene, styrene/ethylene/butylene/styrene or styrene/ethylene/propylene/styrene.
3. Graft copolymers of styrene or α-methylstyrene such as, for example, styrene on polybutadiene, styrene on polybutadiene-styrene or polybutadiene-acrylonitrile; styrene and acrylonitrile (or methyacrylonitrile ) on polybutadiene; styrene and maleic anhydride or maleimide on polybutadiene; styrene, acrylonitrile and maleic anhydride or maleimide on polybutadiene; styrene, acrylonitrile and methyl methacrylate on polybutadiene, styrene, acrylonitrile and methyl methacrylate on polybutadiene, styrene and acrylonitrile on ethylene/propylene/diene terpolymers, styrene and acrylonitrile on polyacrylates or polymethacrylates, styrene and acrylonitrile on acrylate/-butatdiene copolymers, as well as mixtures thereof with the copolymers listed under 5), for instance the copolymer mixtures known as ABS-, MBS-, ASA- or AES-polymers.
4. Polymers which are derived from α,β-unsaturated acids and derivatives thereof, such as polyacrylates and polymethacrylates, polyacrylamide and polyacrylonitrile.
5. Copolymers from the monomers mentioned under 4), with each other or with other unsaturated monomers, such as, for instance, acrylonitrile/butadiene, acrylonitrile/alkyl acrylate, acrylonitrile/alkoxyalkyl acrylate or acrylonitrile/vinyl halogenide copolymers or acrylonitrile/alkyl methacrylate/butadiene terpolymers, or maleic anhydride/styrene/methyl methacrylate copolymers.

6. Polyphenylene oxides and sulfides, and mixtures or blends of polyphenylene oxides with polystyrene, graft polymers or styrene copolymers e.g. high-impact strength polystyrene, and EPDM copolymers with rubbers, and mixtures of polyphenylene oxides with polyamides.

7. Polyurethanes which are derived from polyethers, polyesters or polybutadienes with terminal hydroxyl groups on the one side and aliphatic or aromatic polyisocyanates on the other side, as well as precursors thereof (polyisocyanates, polyols or prepolymers).

8. Polyamides and copolyamides which are derived from diamines and dicarboxylic acids and/or from aminocarboxylic acids or the corresponding lactams, such as polyamide 4, polyamide 6, polyamide 6/6, 6/10, 6/9, 6/12 and 4/6, polyamide 11, polyamide 12, aromatic polyamides obtained by condensation of m-xylene, diamine and adipic acid; polyamides prepared from hexamethylene diamine and isophthalic or/and terephthalic acid and optionally an elastomer as modifier, for example poly-2,4,4,-trimethyl-hexamethylene terphthalamide or poly-m-phenylene isophthalamide. Further copolymers of the aforementioned polyamides with polyolefins, olefin copolymers, ionomers or chemically bonded or grafted elastomers; or with polyethers, such as, for instance, with polyethylene glycol, polypropylene glycol or polytetra-methylene glycols. Polyamides or copolyamides modified with EPDM or ABS. Polyamides condensed during processing (RIM-polyamide systems).

9. Polyesters which are derived from dicarboxylic acids and diols and/or from hydroxycarboxylic acids or the corresponding lactones, such as polyethylene terephthalate, polybutylene terephthalate, poly-1,4-dimethylol-cyclohexane terephthalate, poly-[2,2,-)4-hydroxyphenyl)propane]terephthalate and polyhydroxybenzoates as well as block-copolyether-esters derived from polyethers having hydroxyl end groups.

10. Polycarbonates and polyester-carbonates.

11. Crosslinkable epoxy resins which are derived from polyepoxides, for example from bis-glycidyl ethers or from cycloaliphatic di-epoxides.

The polymer is preferably polystyrene, especially high-impact polystyrene, an acrylonitrile-butadiene-styrene polymer optionally blended with a polycarbonate, blend of polyphenylene oxide with high impact polystyrene, a polyester, a polyamide or an epoxy resin.

The proportion by weight of flame retardant compound of formula I is conveniently within the range of from 0.1 to 50% by weight, more preferably from 0.5 to 30% by weight of the polymer.

The compositions of the invention may also contain other conventional ingredients, such as heat stabilisers, light stabilisers, ultraviolet light absorbers, anti-oxidants, anti-static agents, preservatives, adhesion promotors, fillers, fibre reinforcement, pigments, lubricants, blowing agents, fungicides, plasticisers, processing aids, anti-dripping agents e.g. fluorinated polyolefins such as polytetrafluoroethylenes, other fire-retardant additives and smoke suppressants.

The flame retardant additive of formula I is preferably used in conjunction with a further flame retardant. Examples of such further flame retardants are the oxides, sulphides, sulphates, halides, oxyhalides and borates of tin, iron, molybdenum, zinc and antimony e.g. tin oxide, iron oxide, molybdenum oxide, zinc oxide, antimony oxide and zinc borate; metal stannates e.g. magnesium calcium and zinc stannates phosphorus-containing esters and salts e.g. triaryphosphates, alkylarylphosphates and ammonium polyphosphates; halogen-, especially bromine- and chlorine-containing compounds e.g. decabromodiphenylether, hexachlorocyclopentadiene, brominated polystyrene, halogenoalkyl phosphates and -phosphonate esters; metal hydrates especially hydrated alumina; and the dehydropolymers of compounds of mono-, di- or td-substituted benzene, the substituents being a C5- and/or C6-cycloaliphatic hydrocarbon, especially 1,1-diphenylbicyclohexyl or 1,1-diphenylbicyclopentyl, as disclosed in DE-PS 2525697. The preferred further flame retardant is antimony oxide.

The further flame retardant is conveniently employed in the composition of the present invention in an amount within the range of from 1 to 15%, especially from 2 to 10% by weight, based on the weight of the polymer.

The following Examples further illustrate the present invention.

Example 1—Hexabromodiphenyldianhydride

In a 1 liter, 3 necked flask fitted with condenser, temperature probe, bromine addition funnel and magnetic stirrer bar, is placed 75.24 g diphenyldianhydride (DPDA), 1 g iodine, 1 g iron, and 590 ml oleum (30% $SO_3$). The solution is warmed to reflux and 136.58 g $Br_2$ is weighed into the dropping funnel. Bromine is added over 5 hours keeping excess refluxing vapor to a minimum. The reaction mixture is cooled and filtered. The solid product is washed with $H_2SO_4$, then re-slurried in 1 liter water and the pH adjusted to 14 with 100 ml of 50% NaOH solution. The suspension is filtered, 500 ml of ethyl acetate is added to the flitrate and the pH reduced to 0.2 with 150 ml concentrated HCl. This mixture is stirred for 2 hours at 35° C. The aqueous phase is separated from ethyl acetate phase and the latter is washed with 1N HCl, then $H_2O$. Ethyl acetate is evaporated under vacuum to yield a white powder which is dried in vacuo at 150° C. to give 130 g product (66% yield).

Examples 2 to 5

The product from Example 1 with the addition of antimony oxide is compounded into HIPS (high impact polystyrene poly-grade, 464 from Huntsman) and ABS (acrylonitrile-butadiene-styrene polymer-Magnum 35B from DOW) in the proportions given in the table below, based on 100 parts by weight of polymer.

Compounding is performed using a torque rheometer at a temperature of 180° C. and a mixing time of 8 minutes. Test specimens are prepared from the compounded product by compression molding at 200° C.

The Limiting Oxygen Index (L.O.I) of the specimen is measured according to the method of ASTM 2863-87 standard and the flammability of the specimen is tested according to the method of "Test for Flammability of Plastics Materials" Underwriter Laboratories Subject 94 (UL94) standard at a specimen thickness of 3.2 mm.

Results are shown for controls also, wherein the products from Example 1 and 2 and the antimony oxide were excluded.

In the UL94 standard, 94V-0 in the highest rating, followed by 94V-1 and 94V-2 in descending order. "Freely burned" (FB) indicates failure to meet any of these ratings.

| Example | Product of Ex. 1 (phr) | Antimony Oxide (phr) | POLYMER | LOI (%) | UL94 |
| --- | --- | --- | --- | --- | --- |
| 2 | 12 | 2.48 | ABS | 23.7 | V-O |
| 3 | 20 | 4.14 | ABS | 25.5 | V-O |
| 4 | 12 | 2.48 | HIPS | 22.5 | V-O |
| 5 | 20 | 4.14 | HIPS | 25.4 | V-O |
| — | — | — | ABS | 18.0 | FB |
| — | — | — | HIPS | 17.6 | FB |

We claim:

1. A compound characterized by the general formula I

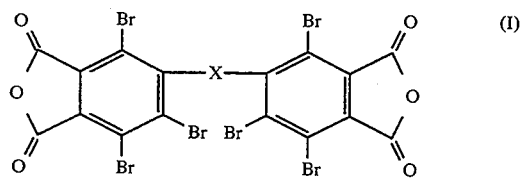

in which X represents a direct bond or a

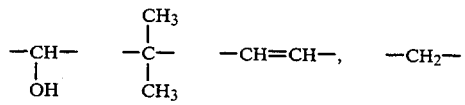

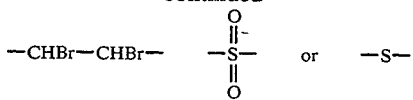

group.

2. A compound as claimed in claim 1 characterized in that X represents a direct bond.

3. A flame retarded plastics or rubber composition comprising as the flame retardant a compound of general formula I as claimed in claim 1 or 2.

4. A composition as claimed in claim 3 characterized in that the plastics or rubber is a polymer selected from an ABS copolymer, high impact polystyrene or other engineering plastics material.

5. A composition as claimed in claim 3 characterized in that the amount of compound of formula I is from 0.1 to 50% by weight, based on the weight of the plastics or rubber component of said composition.

6. A composition as claimed in claim 5 characterized in that the amount of compound of formula I is from 0.5 to 30% by weight.

7. A composition as claimed in claim 3 characterized in that it also contains another flame retardant.

8. A composition as claimed in claim 3 characterized in that the other flame retardant is antimony oxide.

9. A composition as claimed in claim 7 characterized in that the amount of other flame retardant is from 1 to 15% by weight based on the weight of the plastics or rubber component of said composition.

10. A composition as claimed in claim 9 characterized in that the amount of other flame retardant is from 2 to 10% by weight.

11. A composition as claimed in claim 8 wherein the amount of the antimony oxide is from 1 to 15% by weight based on the weight of the plastics or rubber component of said composition.

12. A composition as claimed in claim 11 wherein the amount of the antimony oxide is from 2 to 10% by weight based on the weight of the plastics or rubber component of said composition.

* * * * *